US010154993B2

(12) United States Patent
Uchida et al.

(10) Patent No.: US 10,154,993 B2
(45) Date of Patent: Dec. 18, 2018

(54) SOLID PHARMACEUTICAL COMPOSITION (71) Applicant: KYORIN PHARMACEUTICAL CO., LTD., Tokyo (JP)

(72) Inventors: Hiroshi Uchida, Tochigi (JP); Masataka Hanada, Tochigi (JP); Yoshikazu Miyazaki, Tochigi (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/519,917

(22) PCT Filed: Oct. 23, 2015

(86) PCT No.: PCT/JP2015/005341
§ 371 (c)(1),
(2) Date: Apr. 18, 2017

(87) PCT Pub. No.: WO2016/063542
PCT Pub. Date: Apr. 28, 2016

(65) Prior Publication Data
US 2017/0319571 A1   Nov. 9, 2017

(30) Foreign Application Priority Data
Oct. 23, 2014   (JP) ................................ 2014-216516

(51) Int. Cl.
*A61K 31/4709* (2006.01)
*A61K 47/02* (2006.01)
*A61K 47/26* (2006.01)
*A61K 9/16* (2006.01)
*A61K 9/20* (2006.01)

(52) U.S. Cl.
CPC .......... *A61K 31/4709* (2013.01); *A61K 9/16* (2013.01); *A61K 9/2009* (2013.01); *A61K 9/2013* (2013.01); *A61K 9/2018* (2013.01); *A61K 9/2095* (2013.01); *A61K 47/02* (2013.01); *A61K 47/26* (2013.01)

(58) Field of Classification Search
CPC .... A61K 31/4709; A61K 47/26; A61K 47/02; A61K 9/16; A61K 9/2095; A61K 9/2009; A61K 9/2013; A61K 9/2018
See application file for complete search history.

(56) References Cited

U.S. PATENT DOCUMENTS

| | | | |
|---|---|---|---|
| 4,897,270 A | 1/1990 | Deutsch et al. | |
| 6,727,243 B1 | 4/2004 | Jennewein et al. | |
| 7,514,451 B2 * | 4/2009 | Asahina | C07D 401/04 514/300 |
| 8,969,379 B2 | 3/2015 | Furitsu et al. | |
| 9,090,587 B2 * | 7/2015 | Araya | C07D 401/04 |
| 9,504,746 B2 | 11/2016 | Furitsu et al. | |
| 9,603,804 B2 * | 3/2017 | Uchida | B01F 3/04446 |
| 9,687,453 B2 * | 6/2017 | Uchida | A61K 31/4709 |
| 2004/0082593 A1 | 4/2004 | Sommermeyer et al. | |
| 2004/0224014 A1 | 11/2004 | Badwan et al. | |
| 2006/0024361 A1 * | 2/2006 | Odidi | A61K 9/2018 424/464 |
| 2006/0281779 A1 | 12/2006 | Asahina et al. | |
| 2008/0031942 A1 | 2/2008 | Uchiyama et al. | |
| 2009/0117205 A1 | 5/2009 | Yano et al. | |
| 2014/0288310 A1 | 9/2014 | Araya et al. | |
| 2016/0074330 A1 | 3/2016 | Uchida et al. | |

FOREIGN PATENT DOCUMENTS

| | | |
|---|---|---|
| JP | 2006-298811 | 11/2006 |
| JP | 2013-43834 | 3/2013 |
| WO | 99/44614 | 9/1999 |
| WO | 02/067943 | 9/2002 |
| WO | 2005/026147 | 3/2005 |
| WO | 2005026147 | * 3/2005 |
| WO | 2013/069297 | 5/2013 |
| WO | 2013069297 | * 5/2013 |
| WO | 2013/145749 | 10/2013 |
| WO | 2013/145750 | 10/2013 |
| WO | 2013145750 | * 10/2013 |
| WO | 2014/174847 | 10/2014 |
| WO | 2014147848 | * 10/2014 |

OTHER PUBLICATIONS

Sano, Int J Pharm, vol. 416, 252-259, 2011. (Year: 2011).*
Bhandari, CA 155:624222, abstract only of Industrial & Engineering Chem Res, 50(22), 12784-12789, 2011. (Year: 2011).*
Saxena, CA162:195878, abstract only of Int J Harm Sci and Res, 4(8), 3110-3124, 2013. (Year: 2013).*
Brown, Drug Development & Delivery, vol. 3 (6), 2003, 1-4. (Year: 2003).*
Khinchi, J App PHarm Sc, vol. 1(1), 50-58, 2011. (Year: 2011).*
International Search Report dated Jan. 12, 2016 in International Application No. PCT/JP2015/005341.
Takeshi Hamaura et al., "Decrease in Dissolution of Cefpodoxime Proxetil Tablets by Gel Formation and Its Improvement", Journal of Pharmaceutical Science and Technology, Japan, vol. 55, No. 3 (1995), pp. 175-182.

(Continued)

*Primary Examiner* — D Margaret M Seaman
(74) *Attorney, Agent, or Firm* — Wenderoth, Lind & Ponack, L.L.P.

(57) ABSTRACT

[Problem] To provide a novel pharmaceutical composition which can suppress delayed, release of the compound represented in general formula (1) or a salt thereof.

[Solution] This solid pharmaceutical composition contains the compound represented in general formula (1), or a salt thereof, and a salting-out agent.

17 Claims, 3 Drawing Sheets

(56) References Cited

OTHER PUBLICATIONS

Takeshi Hamaura, "Gel formation of cefpodoxime proxetil, basic antibiotic and its formulation design", Pharm Tech Japan, vol. 17, No. 4 (2001) 87-100 (619-632).
International Preliminary Report on Patentability and Written Opinion of the International Searching Authority dated May 4, 2017 in corresponding International (PCT) Application No. PCT/JP2015/005341.

* cited by examiner

| No. | 2θ | RELATIVE INTENSITY | INTENSITY |
|---|---|---|---|
| 1 | 7.9 | vs | 4961 |
| 2 | 9.8 | m | 872 |
| 3 | 10.5 | s | 2155 |
| 4 | 11.6 | s | 2258 |
| 5 | 12.2 | vs | 4976 |
| 6 | 12.3 | m | 823 |
| 7 | 14.4 | m | 1305 |
| 8 | 14.7 | s | 1913 |
| 9 | 15.7 | m | 775 |
| 10 | 15.8 | m | 940 |
| 11 | 16.4 | m | 945 |
| 12 | 16.9 | m | 772 |
| 13 | 17.1 | m | 717 |
| 14 | 17.3 | m | 1140 |
| 15 | 18.8 | s | 2855 |
| 16 | 19.3 | w | 485 |
| 17 | 19.3 | w | 310 |
| 18 | 19.5 | m | 528 |
| 19 | 19.7 | m | 610 |
| 20 | 19.9 | w | 302 |
| 21 | 20.2 | m | 718 |
| 22 | 21.2 | s | 1990 |
| 23 | 21.6 | m | 1355 |
| 24 | 22.1 | s | 2930 |
| 25 | 22.4 | m | 757 |
| 26 | 23.4 | m | 1393 |
| 27 | 23.9 | m | 852 |
| 28 | 24.2 | m | 838 |
| 29 | 24.4 | s | 2484 |
| 30 | 25.0 | m | 1038 |
| 31 | 25.3 | w | 470 |
| 32 | 25.5 | m | 695 |
| 33 | 25.8 | m | 683 |
| 34 | 26.0 | m | 997 |
| 35 | 26.4 | s | 1955 |
| 36 | 26.8 | m | 1677 |
| 37 | 27.3 | m | 992 |
| 38 | 27.8 | m | 715 |
| 39 | 28.3 | m | 717 |
| 40 | 29.0 | w | 395 |
| 41 | 29.5 | m | 610 |
| 42 | 30.3 | w | 330 |
| 43 | 31.6 | m | 615 |
| 44 | 32.2 | m | 563 |
| 45 | 32.5 | w | 405 |
| 46 | 32.8 | m | 643 |
| 47 | 33.1 | w | 402 |
| 48 | 33.6 | m | 835 |
| 49 | 34.0 | w | 335 |
| 50 | 34.4 | w | 358 |
| 51 | 34.8 | m | 593 |
| 52 | 35.4 | m | 510 |
| 53 | 36.1 | w | 383 |
| 54 | 36.5 | w | 453 |
| 55 | 36.8 | w | 435 |
| 56 | 39.0 | m | 625 |
| 57 | 39.3 | w | 380 |

DEFINITION
%RELATIVE INTENSITY(ri)    DEFINITION
  $50 \leq ri \leq 100$       vs (VERY HIGH)
  $20 \leq ri < 50$           s (HIGH)
  $5 \leq ri < 20$            m (MIDDLE)
  $0.7 \leq ri < 5$           w (LOW)
  $ri < 0.7$                  vw (VERY LOW)

SOLID PHARMACEUTICAL COMPOSITION

TECHNICAL FIELD

The present invention relates to a solid pharmaceutical composition containing a compound represented by general formula (1) or a salt thereof.

[Chemical Formula 1]

(1)

In formula (1), $R^1$ represents an alkyl group having 1 to 3 carbon atoms which one or two or more hydrogen atoms may be substituted with a halogen atom, an amino group, or a cyano group, $R^2$ represents an alkyl group having 1 to 3 carbon atoms, a hydrogen atom, a halogen atom, a hydroxyl group, or an amino group, $R^3$ represents a hydrogen atom or a halogen atom, $R^4$ represents a hydrogen atom ox a fluorine atom, and X represents a halogen atom.

BACKGROUND ART

Some pharmaceutically active components which cause gelation under a certain condition have been known (Patent Literatures 1 to 7 and Non-Patent Literatures 1 and 2). In general, when a solid dosage form is orally administrated, the solid dosage form readily disintegrates in the gastrointestinal tract to dissolve a pharmaceutically active component, whereby the pharmaceutically active component is absorbed into the body. However, when a solid dosage form containing a pharmaceutically active component which, causes gelation is administrated, there arises such a problem that gelation of the active pharmaceutical ingredient delays the disintegration of the solid dosage form, and delays the dissolution of the pharmaceutically active ingredient.

As conventional techniques of improving delayed disintegration due to gelation, a method of adding cyclodextrin to suppress gel formation or secure the water permeability of a gel layer (Non-Patent Literatures 1 and 2), a method of adding a disintegrant (Non-Patent Literature 1), a method of adding a silicic acid or a silicate (Patent Literatures 1 to 3), a method of making a drug finer and causing the drug to be adsorbed to a carrier (Patent Literature 4), a method in which a film coating is rapidly broken to disintegrate a drug-containing core before gelation (Patent Literature 5), a method using an acidic or basic additive (Patent Literature 6), a method of achieving a form of molecular dispersion such as dispersion of a drug in a polymer (Patent Literature 7), and a method of adding a sugar alcohol (Patent Literatures 8 to 10) have been known.

Further, as a dosage form containing a quinolone carboxylic acid antimicrobial agent in which a main drug is stabilized, an oral composition containing an acidic additive (Patent Literature 11) and a dosage form for injection containing an acidic additive (Patent Literatures 12 and 13) have been known.

CITATION LIST

Patent Literature

Patent Literature 1: JP2006-298811
Patent Literature 2: WO2006/030826
Patent Literature 3: JP2002-505290
Patent Literature 4: JP2004-522782
Patent Literature 5: JP1987-123118
Patent Literature 6: WO2006/059716
Patent Literature 7: JP2002-530338
Patent Literature 8: WO2013/145749
Patent Literature 9: WO2013/145745
Patent Literature 10: JP2013-43334
Patent Literature 11: JP2004-339198
Patent Literature 12: JP2004-509921
Patent Literature 13: WO2006/004028

Non-Patent Literature

Non-Patent Literature 1: Journal of Pharmaceutical Science and Technology, Japan, Vol. 55, No. 3 (1993), pp. 175-182
Non-Patent Literature 2: Pharm Tech Japan, vol. 17, No. 4 (2001), pp. 87-100 (619-632)

SUMMARY OF INVENTION

Technical Problem

The present invention provides a novel pharmaceutical composition which can suppress delayed release of a compound represented by general formula (1) or a salt thereof due to gelation.

[Chemical Formula 2]

(1)

In formula (1), $R^1$ represents an alkyl group having 1 to 3 carbon atoms which one or two or more hydrogen atoms may be substituted with a halogen atom, an amino group, or a cyano group, $R^2$ represents an alkyl group having 1 to 3 carbon atoms, a hydrogen atom, a halogen atom, a hydroxyl group, or an amino group, $R^3$ represents a hydrogen atom or a halogen atom, represents a hydrogen atom or a fluorine atom, and X represents a halogen atom.

Solution to Problem

The inventors of the present invention have found that when a solid pharmaceutical composition contains a compound represented by general formula (1) or a salt thereof together with a salting-out agent, delayed release of the compound represented by general formula (1) can be suppressed. The present invention has thus been completed.

The summary of the present invention is as follows:

[1] A solid pharmaceutical composition containing a compound represented by general formula (1):

[Chemical Formula 3]

(1)

(wherein $R^1$ represents an alkyl group having 1 to 3 carbon atoms which one or two or more hydrogen atoms may be substituted with a halogen atom, an amino group, or a cyano group, $R^2$ represents an alkyl group having 1 to 3 carbon atoms, a hydrogen atom, a halogen atom, a hydroxyl group, or an amino group, $R^3$ represents a hydrogen atom or a halogen atom, $R^4$ represents a hydrogen, atom ox a fluorine atom, and X represents a halogen atom)
or a salt thereof, and a salting-out agent.

[2] The solid pharmaceutical composition according to [1], further containing a non-cellulosic excipient.

[3] The solid pharmaceutical composition according to [2], wherein the solid pharmaceutical composition is obtained by compression-molding a mixture including
(i) a granulated substance containing the compound represented by general formula (1) or a salt thereof and the non-cellulosic excipient, and
(ii) the salting-out agent.

[4] The solid pharmaceutical, composition according to any one of [1] to [3], further containing a disintegrant.

[5] The solid pharmaceutical composition according to [4], containing a swelling disintegrant as the disintegrant.

[6] The solid pharmaceutical composition according to [2], wherein the solid pharmaceutical composition is obtained by directly compression-molding a mixture including the compound represented by general formula (1) or a salt thereof, the non-cellulosic excipient, and the salting-out agent.

[7] The solid pharmaceutical composition according to [6], containing a sugar alcohol as the non-cellulosic excipient.

[8] The solid pharmaceutical composition according to [6] or [7] containing isomalt and/or xylitol as the non-cellulosic excipient.

[9] The solid pharmaceutical composition according to any one of [6] to [8], containing sodium chloride as the salting-out agent.

[10] The solid pharmaceutical composition according to any one of [1] to [9], containing a hydrochloride as the salt of the compound represented by general formula (1).

[11] A method for producing the solid pharmaceutical composition according to [2], wherein the solid pharmaceutical composition is a tablet, and wherein the method including:

(i) mixing a granulated substance containing the compound represented by general formula (1) or a salt thereof and the non-cellulosic excipient with the salting-out agent; and
(ii) compression-molding the obtained mixture,

[12] A method for producing the solid pharmaceutical composition according to [2], wherein the solid pharmaceutical composition is a tablet, and wherein the method including:
(i) mixing the compound represented by general formula (1) or a salt thereof, the non-cellulosic excipient, and the salting-out agent; and
(ii) compression-molding the mixture.

[13] A solid pharmaceutical composition containing:
a granular substance containing a compound represented by general formula (1):

[Chemical Formula 4]

(1)

(wherein $R^1$ represents an alkyl group having 1 to 3 carbon atoms which one or two or more hydrogen atoms may be substituted with a halogen atom, an amino group, or a cyano group, $R^2$ represents an alkyl group having 1 to 3 carbon atoms, a hydrogen atom, a halogen atom, a hydroxyl group, or an amino group, $R^3$ represents a hydrogen atom or a halogen atom, $R^4$ represents a hydrogen atom or a fluorine atom, and X represents a halogen atom)
or a salt thereof and a non-cellulosic excipient; and
a salting-out agent,

[14] A solid pharmaceutical composition containing a compound represented by general formula (1):

[Chemical Formula 5]

(1)

(wherein $R^1$ represents an alkyl group having 1 to 3 carbon atoms which may be substituted with one or two or more of a halogen atom, an amino group, or a cyano group, $R^3$ represents an alkyl group having 1 to 3 carbon atoms, a hydrogen atom, a halogen atom, a hydroxyl group, or an amino group, $R^3$ represents a hydrogen atom or a halogen atom, R⁴ represents a hydrogen atom or a fluorine atom, and X represents a halogen atom)
or a salt thereof, a non-cellulosic excipient, and a salting-out agent, wherein the composition is substantially uniform.

Advantageous Effects of Invention

The present invention can provide a novel pharmaceutical composition which can suppress delayed release of a compound represented by general formula (1) era salt thereof due to gelation.

DESCRIPTION OF EMBODIMENTS

Hereinafter, one of embodiments of the present invention will be described in detail.

This embodiment relates to a solid pharmaceutical composition containing a compound represented by general formula (1) or a salt thereof and a salting-out agent.

The solid pharmaceutical composition herein means a pharmaceutical composition including a solid component to be contained.

[Chemical Formula 6]

(1)

In formula (1), $R^1$ represents an alkyl group having 1 to 3 carbon atoms, $R^2$ represents an alkyl group having 1 to 3 carbon atoms, a hydrogen atom, a halogen atom, a hydroxyl group, or an amino group, $R^3$ represents a hydrogen atom or a halogen atom, $R^4$ represents a hydrogen atom or a fluorine atom, and X represents a halogen atom. Regarding the alkyl group having 1 to 3 carbon atoms represented by $R^1$, one or two or more hydrogen atoms may toe substituted with one or two or more of a halogen atom, an amino group, or a cyano group.

The "halogen atom" described herein means a fluorine atom, a chlorine atom, a bromine atom, or an iodine atom. In general formula (1), the halogen atom is preferably a fluorine atom. The "alkyl group having 1 to 3 carbon atoms" described herein means a methyl group, an ethyl group, a propyl group, or a 2-propyl group.

The compound represented by general formula (1) or a salt thereof to be contained in the solid pharmaceutical composition of this embodiment can be produced, for example, by a method described in WO 2005/026147. The compound represented by general formula (1) to be contained in the solid pharmaceutical composition of this embodiment is preferably
7-[3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid, and more preferably
7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquin oline-3-carboxylic acid.

It is preferable that the solid pharmaceutical composition of this embodiment contain a salt of the compound represented by general formula (1) from the viewpoint of improvement in solubility in water.

The salt of the compound represented by general formula (1) that can be contained in the solid pharmaceutical composition of this embodiment is not particularly limited as long as it is a pharmaceutically acceptable salt. Examples of the salt of the compound represented by general formula (1) may include salts with inorganic acids such as hydrochloric acid, hydrobromic acid, sulfuric, acid, and phosphoric acid, salts with organic acids such as maleic acid, fumaric acid, succinic acid, malic acid, malonic acid, methanesulfonic acid, toluenesulfonic acid, benzenesulfonic acid, lactic acid, oxalic acid, acetic acid, trifluoroacetic acid, and tartaric acid, and salts with metals such as sodium, potassium, magnesium, calcium, aluminum, cesium, chromium, cobalt, copper, iron, zinc, platinum, and silver. In particular, a hydrochloride is particularly preferred from the viewpoint of stability of the compound. A hydrochloride of the compound represented by general formula (1) is excellent since decomposition of the compound by light irradiation is unlikely to proceed and chemical decomposition is low even in storage under an acceleration test condition, as compared with the compound in a free form represented by general formula (1) and another salt of the compound represented by general formula (1). The salt of the compound represented by general formula (1) which can be contained in the solid pharmaceutical composition of this embodiment is more preferably
7-[3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride, and further more preferably
7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquin oline-3-carboxylic acid hydrochloride.

Figure 1:
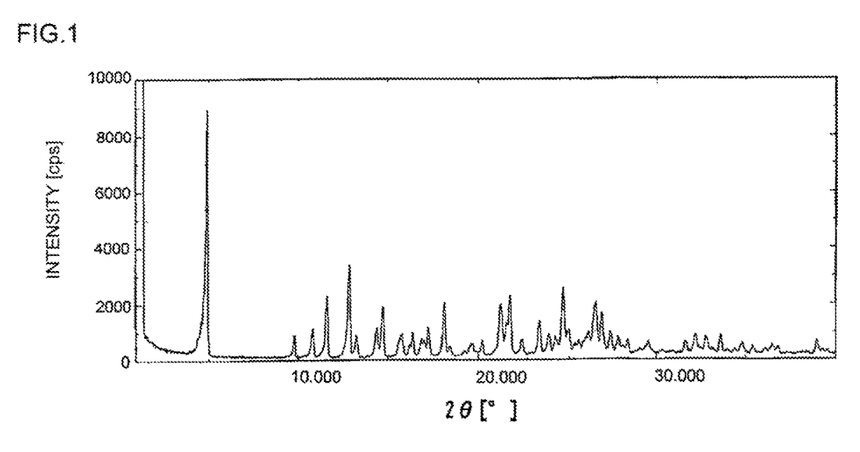
FIG. 1 is an X-ray powder diffraction pattern of 7-[(3S,4S)-3-{(cyclopropylamino) methyl}-4-fluoropyrrolidine-1-yl]-6-fluoro-1-(2-fluoroethyl)-8-methoxy-4-oxo-1,4-dihydroquin oline-3-carboxylic acid hydrochloride A-form crystal.
Figure 2:
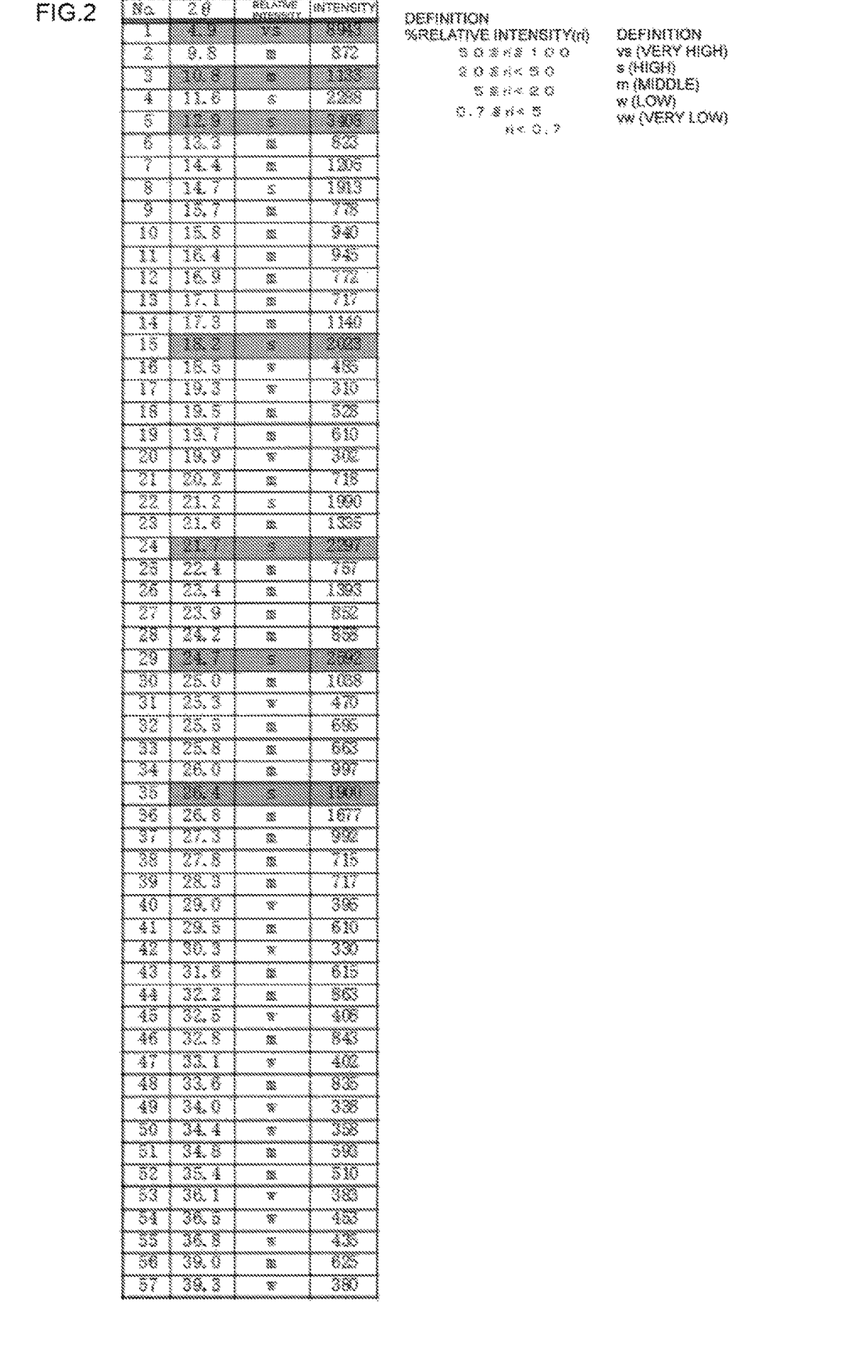
FIG. 2 is a table describing peaks of which the relative intensity is 0.7 or more when the intensity of a peak at a 2θ of 4.9 degrees in the diffraction pattern shown in FIG. 1 is taken as 100.

Among the
7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquin oline-3-carboxylic acid hydrochlorides, a crystal (A-form crystal) having an X-ray powder diffraction pattern with peaks at diffraction angles 2θ of 10.8, 12.9, and 24.7 degrees (±0.2 degrees for each angle) is easy to be gelled when being in contact with water. Therefore, when the A-form crystal is contained in the solid pharmaceutical composition, use of the technique according to this embodiment is useful. The X-ray powder diffraction pattern of the A-form crystal is shown in FIG. 1. FIG. 2 shows a table describing relative intensities of peaks included in the diffraction pattern shown in FIG. 1. For example, the A-form crystal can be produced by a method described in WO2013/069297.

Herein, the X-ray powder diffraction can be performed using RINT2200 manufactured by Rigaku Denki Co., Ltd. Copper radiation (CuKα radiation) is used as radiation. A measurement condition may include a tube current of 36 mA, a tube voltage of 40 kV, a divergence slit of 1 degree, a scattering slit of 1 degree, a receiving slit of 0.15 mm, a scanning range of 1 to 40 degrees (2θ), and a scanning speed of 2 degrees (2θ) per minute.

The content of the compound represented by general formula (1) or the salt thereof in the whole mass of the solid pharmaceutical composition is preferably 10% by mass or more and 75% by mass or less, more preferably 20% by mass or more and 60% by mass or less, particularly preferably 20% by mass or more and 50% by mass or less, and further preferably 35% by mass or more and 45% by mass or less.

When the solid pharmaceutical composition of this embodiment is a tablet, "the whole mass of the solid pharmaceutical composition" means a mass of a whole uncoated tablet. The "uncoated tablet" described herein means a tablet which is obtained by pressing a raw material into a tablet and is in a state before forming a coating.

The solid pharmaceutical composition of this embodiment contains the compound represented by general formula (1) or the salt thereof and a salting-out agent. When the solid pharmaceutical composition of this embodiment contains a salting-out agent, gelation of the compound represented by general formula (1) or the salt thereof can be suppressed, and delayed release can be suppressed.

The "salting-out agent" described herein means a salt exhibiting a salting-out action. The "salting-out action" described herein is an action of preventing a gel substance having high viscosity from being formed by contact of the compound represented by general formula (1) with water. This action may be caused by unstabilizing hydration generated between the compound represented by general formula (1) and water by the salting-out agent.

Examples of the "salting-out agent" to be contained in the solid pharmaceutical composition of this embodiment may include an organic acid salt, an inorganic salt, and a salt of an amino acid.

Examples of the organic acid, salt may include citric salts such as monobasic sodium citrate, dibasic sodium citrate, and sodium citrate, succinates such as disodium succinate, and acetate salts such as calcium acetate and sodium acetate.

Examples of the inorganic salt may include phosphoric salts such as sodium dihydrogen phosphate, disodium monohydrogen phosphate, sodium metaphosphate, trisodium phosphate, monobasic potassium phosphate, dibasic potassium phosphate, sodium polyphosphate, and sodium pyrophosphate, carbonates such as sodium carbonate, sodium bi-carbonate, potassium carbonate, potassium bicarbonate, and ammonium carbonate, metal chlorides such as sodium chloride, potassium chloride, magnesium chloride, and calcium chloride, sodium sulfate, sodium sulfite, sodium bisulfite, and sodium, hydroxide. Metal chlorides are preferred, and sodium chloride is further preferred.

Examples of the salt of an amino acid may include glutamates such as L-glutamic acid hydrochloride and monosodium glutate monohydrate, L-glutamic acid hydrochloride is preferred.

The solid pharmaceutical composition of this embodiment may contain one or two or more kinds of these compounds as a salting-out agent.

As described below, a solid pharmaceutical composition as one example of this embodiment may be obtained in a tablet form by compression-molding a mixture of a granulated substance containing the compound represented by general formula (1) or the salt thereof and an excipient such as a non-cellulosic excipient with the salting-out agent. In this case, the salting-out agent exists outside the granulated substance (granular substance) in the obtained solid pharmaceutical composition. However, the granulated substances may separately contain the same or different kind of salting-out agent. In an aspect where an uncoated tablet contains a plurality of granulated substances, the granulated substances and an additive may be in a mixed state. A part of the granulated substances may be exposed to a surface of the uncoated tablet.

The granulated substance (granular substance) herein means a granular molded body obtained by hardening a solid component.

From the viewpoint of further suppressing delayed release due to gelation, the salting-out agent to be contained in the solid pharmaceutical composition of this embodiment is preferably a citric salt, a glutamate, or a metal chloride, more preferably L-glutamic acid hydrochloride, monobasic sodium citrate, dibasic sodium citrate, or sodium, chloride, and further preferably monobasic sodium citrate.

When the solid pharmaceutical composition is a tablet and is produced using the non-cellulosic excipient by a direct compression method, sodium chloride is preferably used as the salting-out agent from the viewpoint of improving the dissolution rate.

The content of the salting-out agent in the pharmaceutical composition of this embodiment is not particularly limited, and may be appropriately set by those skilled in the art. On the other hand, when the pharmaceutical composition of this embodiment is a tablet, the preferable amount of the salting-out agent may be set as follows from the viewpoint of further suppressing gelation of the compound represented by general formula (1) or the salt thereof and improving the dissolution rate.

1) Case where the solid pharmaceutical composition of this embodiment contains a granulated substance and is obtained by compression-molding a mixture of the granulated substance with another component and the salting-out agent exists outside the granulated substance In this case, the "granulated substance" containing the compound represented by general formula (1) or the salt thereof and the "salting-out agent" are mixed and the mixture is used. The content of the salting-out agent is 0.10 parts by mass or more and 0.50 parts by mass or less relative to 1 part by mass of the granulated substance. The content thereof is more preferably 0.15 parts by mass or more and 0.40 parts by mass or less, and particularly preferably 0.20 parts by mass or more and 0.30 parts by mass or less.

2) Case where the solid pharmaceutical composition of this embodiment contains a granulated substance and is obtained by compression-molding a mixture of the granulated substance with another component and the salting-out agent exists in the granulated substance In this case, the salting-out agent is mixed in the granulated substance. The content of the salting-out agent is preferably 0.05 parts by mass or more and 0.40 parts by mass or less relative to 1 part by mass of the compound represented by general formula (1) or the salt thereof. The content thereof is more preferably 0.10 parts by mass or more and 0.30 parts by mass or less, and particularly preferably 0.10 parts by mass or more and 0.20 parts by mass or less.

3) Case of Using Direct Compression Method

The content of the salting-out agent is preferably 0.20 parts by mass or more and 1.0 part by mass or less relative to 1 part by mass of the compound represented by general formula (1) or the salt thereof. The content thereof is more preferably 0.25 parts by mass or more and 0.70 parts by mass or less, and particularly preferably 0.30 parts by mass or more and 0.50 parts by mass or less.

In addition to the compound represented by general formula (1) or the salt thereof and the salting-out agent, the solid pharmaceutical composition of this embodiment may contain an additive such as an excipient, a disintegrant, a binder, and a lubricant. The additive contained is not particularly limited as long as it can be used in production of a pharmaceutical dosage form. For example, additives described in "Japanese Pharmaceutical Excipients Directory (International Pharmaceutical Excipients Council Japan, YAKUJI NIPPO, LTD. (2007)) can be appropriately used.

The excipient described herein includes a "cellulosic excipient" and a "non-cellulosic excipient."

The "cellulosic excipient" described herein is an excipient containing cellulose or a derivative thereof as a component. The solid pharmaceutical composition of this embodiment may contain as the cellulosic excipient one or two or more kinds of microcrystalline cellulose, carmellose, carmellose calcium, carmellose sodium, croscarmellose sodium, carboxymethyl cellulose calcium, and low substituted hydroxypropylcellulose, for example. Among these, it is preferable that the cellulosic excipient in the solid pharmaceutical composition of this embodiment be microcrystalline cellulose since the hardness of a molded tablet can be made high.

The "non-cellulosic excipient" described herein is an excipient containing a compound having no cellulose skeleton in its structure as a component. Examples thereof may include monosaccharides such as glucose and fructose, disaccharides such as lactose, sucrose, maltose, trehalose, and maltose, starches such as corn starch, and sugar alcohols including monosaccharide alcohols such as mannitol, sorbitol, xylitol, and erythritol, and disaccharide alcohols such as isomalt, maltitol, and lactitol. The solid pharmaceutical composition of this embodiment may contain one or two or more kinds of these excipients.

When the solid pharmaceutical composition is a tablet and is produced using the non-cellulosic excipient through a granulation process, the non-cellulosic excipient is preferably a disaccharide, and more preferably lactose, from the view point of facilitating granulation and compression-molding.

When the solid pharmaceutical composition is a tablet and is produced using the non-cellulosic excipient through a direct compression method, the non-cellulosic excipient is preferably a sugar alcohol from the view point of improving the dissolution rate. The sugar alcohol is more preferably a disaccharide alcohol or a monosaccharide alcohol having a solubility in water at 25° C. of 25% or more. The disaccharide alcohol is more preferably isomalt. The monosaccharide alcohol having a solubility in water at 25° C. of 25% or more is more preferably a monosaccharide alcohol having a solubility of 25% or more and 80% or less. The monosaccharide alcohol having a solubility of 25% or more and 80% or less is sorbitol, xylitol, or erythritol, and particularly preferably xylitol.

The "solubility in water" described herein is a value obtained by calculation using the following equation from the mass (g) of a solute to be dissolved in 100 g of water.

Solubility in water (%)=mass (g) of solute/(100 g+mass (g) of solute)×100

The compound represented by general formula (1) or the salt thereof is decomposed, for example, by pressurization during a production process, to produce a compound represented by the following formula (2) or the like. Use of the non-cellulosic excipient as an excipient is preferred since decomposition of the compound represented by general formula (1) or the salt thereof can be suppressed.

[Chemical Formula 7]

(2)

In formula (2), $R^1$, $R^2$, $R^3$, and X have the same respective definitions as described above.

When the solid pharmaceutical composition of this embodiment contains the compound represented by general formula (1) or the salt thereof, the salting-out agent, and the non-cellulosic excipient, the preferable amount of the non-cellulosic excipient is as follows from the view point of further suppressing the gelation of the compound represented by general formula (1) or the salt thereof and improving the dissolution rate.

1) Case where the solid pharmaceutical composition of this embodiment contains a granulated substance and the non-cellulosic excipient exists outside the granulated substance The content of the non-cellulosic excipient existing outside the granulated substance is preferably 0.1 parts by mass or more and 0.1 parts by mass or less relative to 1 part by mass of the granulated substance. The content thereof is more preferably 0.15 parts by mass or more and 0.6 parts by mass or less, and particularly preferably 0.2 parts by mass or more and 0.5 parts by mass or less.

2) Case where the solid pharmaceutical composition of this embodiment contains a granulated substance and the non-cellulosic excipient exists in the granulated substance The content of the non-cellulosic excipient in the granulated substance is preferably 5% by mass or more and 50% by mass or less relative to the amount of the whole granulated substance. The content thereof is more preferably 5% by mass or more and 40% by mass or less, particularly preferably 5% by mass or more and 30% by mass or less, and further preferably 10% by mass or more and 30% by mass or less.

3) Case of Using Direct Compression Method

When a direct compression method is used, the content of the non-cellulosic excipient is 10% by mass or more and 80% by mass or less relative to the amount of the whole solid pharmaceutical composition. The content thereof is more preferably 20% by mass or more and 75% by mass or less, particularly preferably 40% by mass or more and 70% by mass or less, and further preferably 45% by mass or more and 65% by mass or less.

For example, the solid pharmaceutical composition of this embodiment may be an oral composition containing a disintegrant. From the view point of enhancing the disintegration properties of the pharmaceutical composition, it is preferable that the solid pharmaceutical composition of this embodiment contain the granulated substance containing the compound represented by general formula (1) or the salt thereof, and the disintegrant outside the granulated substance.

The "disintegrant" described herein is classified into a swelling disintegrant and a wicking disintegrant. The swelling disintegrant is preferably used since a composition having higher hardness and lower friability is obtained.

The swelling disintegrant is a disintegrant which absorbs water to swell, thereby causing disintegration of an oral solid dosage form. Examples of the swelling disintegrant may include hydroxypropyl starch, low substituted hydroxypropylcellulose, sodium carboxymethyl starch, croscarmellose, croscarmellose sodium, and crospovidone. Low substituted hydroxypropylcellulose is preferred.

Herein, low substituted hydroxypropylcellulose means hydroxypropyl cellulose or which the content of the hydroxypropoxyl group is 5.0 to 16.0% by weight. The content of the hydroxypropoxy group can be determined by a method described in a section of "low substituted hydroxypropylcellulose" in Japanese Pharmacopoeia Sixteenth Edition.

The wicking disintegrant is a disintegrant which causes disintegration of an oral solid dosage form by a capillary phenomenon. The wicking disintegrant absorbs water through a void to decrease an interparticle bonding force in the oral solid dosage form, thereby disintegrating the oral solid dosage form. Examples of the wicking disintegrant may include carmellose, carmellose sodium, microcrystalline cellulose and carboxymethylcellulose sodium, cellulose acetatephthalate, wheat starch, rice starch, corn starch, potato starch, pregelatinized starch, partly pregelatinized starch, and microcrystalline cellulose. Carmellose is preferred.

For example, the solid pharmaceutical composition of this embodiment may be an oral composition. Specifically, the solid pharmaceutical composition of this embodiment can be an oral solid dosage form such as a tablet, a granule (subtle granule), a capsule, and a powder. A tablet is preferred.

The solid pharmaceutical composition of this embodiment can be produced by a general method according to the dosage form, and the producing method can be appropriately selected by those skilled in the art.

When the solid pharmaceutical composition of this embodiment is a tablet, it is preferable that the composition be produced by a method including a step of producing a granulated substance using a dry granulation method (hereinafter also referred to as method including a dry granulation method) or a direct compression method. The "dry granulation method" described herein is a method in which a raw material powder is compression-molded, crushed, and classified into particles having appropriate size to obtain a granulated substance. The "direct compression method" is a method in which a mixture obtained by adding a needed additive such as an excipient to a raw material containing an active ingredient is molded by compression without a granulation treatment (direct compression-molding) to obtain an uncoated tablet. According to the method including the dry granulation method and the direct compression method, the solid pharmaceutical composition can be obtained without use of water. Therefore, the gelation of the compound represented by general formula (1) or the salt thereof due to an influence of water can be suppressed.

Hereinafter, a content of the solid pharmaceutical composition of this embodiment will be described more specifically with reference to one example of a method for producing the solid pharmaceutical composition of this embodiment in a tablet form, and the scope of the present invention is not restricted by the content.

(General Production Method 1)

1. The following A component and an excipient are mixed. Further, a B component may be mixed. To a powder obtained by the mixing, a lubricant such as stearic acid, a stearate salt (salt of metal such as aluminum, potassium, sodium, calcium, and magnesium), and sodium laurylsulfate may further be added.

A component: the compound represented by formula (1) or the salt thereof

B component: one or two or more kinds of salting-out agents selected from the group consisting of citric salts such as monobasic sodium citrate, dibasic sodium, citrate, and sodium, citrate, succinates such as disodium succinate, acetate salts such, as calcium acetate and sodium acetate, phosphoric salts such as sodium dihydrogen phosphate, disodium monohydrogen phosphate, sodium metaphosphate, trisodium phosphate, monobasic potassium phosphate, dibasic potassium phosphate, sodium polyphosphate, and sodium pyrophosphate, carbonates such as sodium carbonate, sodium bicarbonate, potassium carbonate, potassium bicarbonate, and ammonium carbonate, metal, chlorides such as sodium chloride, potassium chloride, magnesium chloride, and calcium chloride, sodium sulfate, sodium sulfite, sodium bisulfite, sodium hydroxide, and glutamates such as glutamic acid hydrochloride and monosodium glutate monohydrate.

2. For example, granulation is performed in accordance with a dry granulation method. Specifically, the resulting mixture is compression-molded by a compression molding machine such as ROLLER COMPACTOR or a tableting machine (slug machine), and crushed and subjected to size adjustment by a particle sizing apparatus such as ROLLER COMPACTOR or a sieve, to obtain a granulated substance. To the resulting granulated substance, the B component, the following C component, the excipient, or the lubricant may further be added.

C component: one or two or more kinds of disintegrants selected from the group consisting of swelling disintegrants such as hydroxypropyl starch, low substituted hydroxypropylcellulose, sodium carboxymethyl starch, croscarmellose, croscarmellose sodium, and crospovidone, and wicking disintegrants such as carmellose, carmellose sodium, microcrystalline cellulose and carboxymethylcellulose sodium, cellulose acetate phthalate, wheat starch, rice starch, corn starch, potato starch, pregelatinized starch, partly pregelatinized starch, and microcrystalline cellulose.

3. The resulting granulated substance or a mixture of the granulated substance with the additive is pressed using a tableting machine to obtain a tablet (uncoated tablet). After the pressing into a tablet, the resulting uncoated tablet may be coated with a coating agent such as hypromellose and kollicoat IR.

(General Production Method 2)

1. The following A component and an excipient are mixed. As the excipient, a D component (non-cellulosic excipient) is preferably used. In addition to the A component and the excipient, the B component, (salting-out agent) may be mixed. To a powder obtained by the mixing, a lubricant may be further added.

A component: the compound represented by formula (1) or the salt thereof

D component: one or two or more kinds of non-cellulosic excipients selected from the group consisting of monosaccharides such as glucose and fructose, disaccharides such as lactose, sucrose, maltose, trehalose, and maltose, starches such as corn starch, and sugar alcohols including monosaccharide alcohols such as mannitol, sorbitol, xylitol, and erythritol, and disaccharide alcohols such as isomalt, maltitol, and lactitol.

2. For example, granulation is performed in accordance with a dry granulation method. Specifically, the resulting mixture is compression-molded by a compression molding machine such as ROLLER COMPACTOR or a tableting machine (slug machine), and crushed and subjected to sire adjustment by a particle sizing apparatus such as ROLLER GRANULATOR or a sieve, to obtain a granulated substance. To the resulting granulated substance, the B component (salting-out agent), the C component (disintegrant), the excipient, or the lubricant may further be added.

3. The resulting granulated substance or a mixture of the granulated substance with the additive is pressed using a tableting machine to obtain a tablet (uncoated tablet). After the pressing into a tablet, the resulting uncoated tablet may be coated with a coating agent such as hypromellose and kollicoat IR.

(General Production Method 3)

1. The A component, the B component (salting-out agent), and an excipient are mixed. As the excipient, the D component (non-cellulosic excipient) is preferably used. To a powder obtained by the mixing, a lubricant may further be added.

2. The resulting mixture is pressed using a tableting machine to obtain a tablet (uncoated tablet). The resulting uncoated tablet is in a state of uniform composition. The uniform composition used herein represents that components contained are substantially uniformly dispersed.

After the pressing into a tablet, the resulting uncoated tablet may be coated with a coating agent such as hypromellose and kollicoat IR.

EXAMPLES

Hereinafter, the present invention will be described more in detail with reference to Examples, but the scope of the present invention is not restricted by these Examples.

In the following Examples, an NMR spectrum was measured by JEOL JNM-EX400 nuclear magnetic resonance spectrometer, using tetramethylsilane (TMS) as an internal standard. A MS spectrum was measured by JEOL JMS-T100LP and JMS-SX102A mass spectrometers. Elementary analysis was performed by YANACO CHN CORDER MT-6 elemental analyzer.

X-ray powder diffraction was performed by RINT2200 manufactured by Rigaku Denki Co., Ltd. Copper radiation was used as radiation. As a measurement condition, a tube current of 36 mA, a tube voltage of 40 kV, a divergence slit of 1 degree, a scattering slit of 1 degree, a receiving slit of 0.15 mm, a scanning range of 1 to 40 degrees (2θ), and a scanning speed of 2 degrees (2θ) per minute were used.

Reference Example 1

Bis(acetato-O)-[6,7-difluoro-1-(2-fluoroethyl)-8-methoxy-4-oxo-1,4-dihydroquinoline-3-carboxylate-O³,O⁴]boron 103 g (1.67 mol) of boric acid (for formation of a catalyst) was added to 21.4 L (225 mol) of acetic anhydride under a nitrogen atmosphere, and the mixture was heated and stirred at 70.0 to 76.9° C. for 30 minutes (at a stirring rate of 69.5 rpm). The mixture was cooled to an inner temperature of 24.6° C., 1.01 kg (16.3 mol) of first additional boric acid was added, and the mixture was stirred at 24.6 to 27.4° C. for 30 minutes. 1.01 kg (16.3 mol) of second additional boric acid was added, and the mixture was stirred at 24.7 to 27.5° C. for 30 minutes. 1.01 kg (16.3 mol) of third additional boric acid was added, and the mixture was stirred at 24.7 to 27.7° C. for 30 minutes. 1.01 kg (16.3 mol) of fourth additional boric acid was added, and the mixture was stirred at 25.4 to 29.4° C. for 30 minutes. In addition, the mixture was stirred at 50.0 to 56.9° C. for 30 minutes, to prepare a boric acid triacetate preparation liquid. To the preparation liquid, 5.50 kg (16.7 mol) of 6,7-difluoro-1-(2-fluoroethyl)-8-methoxy-4-oxo-1,4-dihydroquin oline-3-carboxylic acid ethyl ester was added, and the mixed liquid was stirred at 54.7 to 56.9° C. for 3 hours. The mixed liquid was cooled to 30.0° C., and allowed to stand at room temperature overnight. The mixed liquid was heated to 58.6° C. to dissolve the deposited compound, and 16.5 L of acetone was added to the mixed liquid to obtain a reaction liquid (a).

A mixed liquid of 193 L of water and 33.7 L (555 mol) of ammonia water (28%) was cooled to −0.6° C. under a nitrogen atmosphere. To the mixed liquid, the reaction liquid (a) was added, and the vessel for the reaction liquid (a) was washed with 11.0 L of acetone. The mixture was cooled to 15.0° C., and stirred at 4.3 to 15.0° C., for 1 hour. The deposited crystal was collected by filtration, and washed with 55.0 L of water to obtain 14.1 kg of crude wet crystal. The crude wet crystal was dried under reduced pressure at a setting temperature of 65.0° C. for about 22 hours to obtain 6.93 kg of crude crystal (yield: 96.7%), To the resulting crude crystal, 34.7 L of acetone was added under a nitrogen atmosphere, and the mixture was heated (at hot water setting temperature of 57.0° C.) to dissolve the crude crystal. During the heating, 69.3 L of diisopropyl ether was added dropwise (added amount: 12.0 L) until crystallization. After confirmation of crystallization, the mixture was stirred at 48.3 to 51.7° C. for 15 minutes, the rest of diisopropyl ether was added dropwise, and the mixture was stirred at 45.8 to 49.7° C. for 15 minutes. The mixture was cooled to 15.0° C., and stirred at 6.5 to 15.0° C. for 30 minutes. The deposited crystal was collected by filtration, and washed with 6.93 L of acetone and 13.9 L of diisopropyl ether, to obtain 7.41 kg of wet crystal. The resulting wet crystal was dried under reduced pressure at a setting temperature of 65.0° C. for about 20 hours, to obtain 6.47 kg of bis(acetato-O)-[6,7-difluoro-1-(2-fluoroethyl)-8-methoxy-4-oxo-1,4-dihydroquinoline-3-carboxylate-O³,O⁴] boron (yield: 90.3%).

Elemental Analysis (%): as $C_{17}H_{15}BF_3NO_8$
Calculated value: C, 47.58; H, 3.52; N, 3.26.
Measured value: C, 47.41; H, 3.41; H, 3.20.

¹H-NMR (CDCl₃, 400 MHz) δ: 2.04 (6H, s), 4.21 (3H, d, J=2.9 Hz), 4.88 (2H, dt, J=47.0, 4.4 Hz), 5.21 (2H, dt, J=24.9, 3.9 Hz), 8.17 (1H, t, J=8.8 Hz), 9.10 (1H, s).
ESI MS (positive) m/z: 430 (M+H)⁺.

Reference Example 2

Production of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride A mixed liquid of 3.56 kg (15.4 mol) of (3R,4S)-3-cyclopropylaminomethyl-4-fluoropyrrolidine, 11.7 L (84.2 mol) of triethylamine, and 30.0 L of dimethylsulfoxide was stirred at 23.0 to 26.3° C. for 15 minutes under a nitrogen atmosphere. To the mixed liquid, 6.00 kg (14.0 mol) of bis(acetato-O)-[6,7-difluoro-1-(2-fluoroethyl)-8-methoxy-4-oxo-1,4-dihydroquinoline-3-carboxylate-O³,O⁴] boron was added at 23.0 to 26.3° C. to obtain a reaction liquid. The reaction liquid was stirred at 23.7 to 26.3° C. for 2 hours. To the reaction liquid, 120 L of ethyl acetate was added, 12.0 L of water was added, a solution of 960 g (amount corresponding to 2 mol/L) of sodium hydroxide and 12.0 L of water was added, and the mixture was stirred for 5 minutes. After that, an aqueous layer was separated. To the aqueous layer, 120 L of ethyl acetate was added, and the mixture was stirred for 5 minutes. After that, an ethyl acetate layer was separated. The ethyl acetate layer was collected, 120 L of water was added, and the mixture was stirred for 5 minutes and allowed to stand. After that, an aqueous layer was discarded. The ethyl acetate layer was distilled off under reduced pressure. The resulting residue was dissolved in 60.0 L of 2-propanol, and allowed to stand at room temperature overnight. To the solution, a solution of 5.24 L (62.9 mol) of hydrochloric acid and 26.2 L (amount corresponding to 2 mol/L) of water was added, and the mixture was stirred at 28.2 to 30.0° C. for 30 minutes. The mixture was heated at an external temperature of 55.0° C. After dissolution (dissolution was confirmed at 47.1° C.), the mixture was cooled, resulting in crystallization. The mixture was stirred at 39.9 to 41.0° C. for 30 minutes, cooled (guide: to 20.0° C. at a setting temperature of 7.0° C., and to 20.0° C. or lower at −10.0° C.), and stirred at 2.2 to 10.0° C. for 1 hour. The deposited crystal was collected by filtration, and washed with 60 L of 2-propanol, to obtain 9.57 kg of crude wet crystal of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquin oline-3-carboxylic acid hydrochloride.

Reference Example 3

Method for Producing 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride A-form crystal (Compound 1)

9.57 kg of crude wet crystal of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquin oline-3-carboxylic acid hydrochloride was added to a mixed liquid of 60 L of ethanol and 10.8 h of purified water, and dissolved by heating. This dissolved solution was passed through a filter, and washed with a mixed liquid of 24.0 L of ethanol and 1.20 L of purified water. Dissolution was confirmed, and 96.0 L of heated ethanol (99.5) was added at 71.2 to 72.6° C. The dissolved solution was cooled (hot water setting temperature: 60.0° C.). After confirmation of crystallization (crystallization temperature: 61.5° C.), the solution was stirred at 59.4 to 61.5° C. for 30 minutes. The solution was stepwisely cooled (to 50.0° C. at a hot water setting temperature of 40.0° C., to 40.0° C. at a hot water setting temperature of 30.0° C., to 30.0° C. at a hot water setting temperature of 20.0° C., to 20.0° C. at a setting temperature of 7.0° C., and to 15.0° C. at a setting temperature of −10.0° C., and allowed to stand), and stirred at 4.8 to 10.0° C. for 1 hour. The deposited crystal was collected by filtration, and washed with 30.0 L of ethanol, to obtain 5.25 kg of wet crystal of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquin oline-3-carboxylic acid hydrochloride. The resulting wet crystal was dried under reduced pressure at a setting temperature of 50.0° C. for about 13 hours to obtain 4.83 kg of Compound 1 (yield: 72.6%).

Results of X-ray powder diffraction of Compound 1 based on WO2013/069297 are shown in FIGS. 1 and 2. As understood from FIGS. 1 and 2, peaks are found at 4.9 degrees, 9.3 degrees, 10.8 degrees, 12.9 degrees, 14.7 degrees, 18.2 degrees, 21.7 degrees, 11.4 degrees, 24.7 degrees, and 26.4 degrees, and characteristic peaks are confirmed at 4.9 degrees, 10.8 degrees, 12.9 degrees, 18.2 degrees, 21.7 degrees, 24.7 degrees, and 26.4 degrees. In particular, characteristic peaks are confirmed at 10.8 degrees, 12.9 degrees, and 24.7 degrees.

Elemental Analysis Value (%): as $C_{21}H_{24}F_3N_2O_4HCl$
Calculated value: C, 53.00; H, 5.30; N, 8.83,
Measured value: C, 53.04; H, 5.18; M, 8.83,
¹H NMR (DMSO-d₆, 400 MHz) δ (ppm): 0.77-0.81 (2H, m), 0.95-1.06 (2H, m), 2.80-2.90 (2H, m), 3.21-3.24 (1H, m), 3.35-3.39 (1H, m), 3.57 (3H, s), 3.65-3.78 (3H, m), 4.13 (1H, dd, J=41.8, 13.1 Hz), 4.64-4.97 (3H, m), 5.14 (1H, dd, J=32.7, 15.6 Hz), 5.50 (1H, d, J=53.7 Hz), 7.80 (1H, d, J=13.7 Hz), 8.86 (1H, s), 9.44 (2H, brs), 15.11 (1H, brs).
ESI MS (positive) m/z: 440 (M+H)⁺.

Example 1

In accordance with prescription described in Table 1, Compound 1 crushed for 45 seconds using Wonder Blender (trade name) (WB-1, manufactured by Osaka Chemical Co., Ltd.), and L-glutamic acid hydrochloride were mixed for 3 minutes using a pestle and a mortar. The obtained mixture and microcrystalline cellulose were mixed for 3 minutes in a polyethylene bag. To the mixture, sodium stearate fumarate was added, and the mixture was mixed for 30 seconds in the polyethylene bag. The mixture was compression-molded, using a tableting machine (HT-AP-18SS-II, manufactured by Hata Tekkosho Co., Ltd., mortar with a diameter of 8.5 mm, punch with a R plane having a radius of curvature of 10 mm) so that the mass was 200 mg, and the molded substance was then crushed using a pestle and a mortar, to obtain a granulated substance. In the resulting granulated substance, granules which were passed through a 850-μm sieve, and left on a 106-μm sieve were obtained as main drug granules. The main drug granules, microcrystalline cellulose, and low-substituted hydroxypropylcellulose were then mixed for 3 minutes in a polyethylene bag. To the mixture, magnesium stearate was added, and the mixture was mixed for 30 seconds in the polyethylene bag. The mixture was pressed into a tablet using a tableting machine (HT-AP-18SS-II, manufactured by Hata Tekkosho Co., Ltd., mortar with a diameter of 8.5 mm, punch with a R plane having, a radius of curvature of 10 mm) so that the mass was 250 mg and the thickness of a table was 4.2 mm, to obtain a tablet (unseated tablet).

Example 2

In accordance with prescription in described Table 1, the same operation as that in Example 1 was performed except that monobasic sodium citrate was used in place of L-glutamic acid hydrochloride.

Example 3

In accordance with prescription described in Table 1, the same operation as that in Example 1 was performed except that dibasic sodium citrate was used in place of L-glutamic acid hydrochloride.

Comparative Example 1

In accordance with prescription described in Table 1, Compound 1 crushed for 45 seconds using Wonder Blender (trade name) (WB-1, manufactured by Osaka Chemical Co., Ltd.), and microcrystalline cellulose were mixed for 3 minutes in a polyethylene bag. To the mixture, sodium stearate fumarate was added, and the mixture was mixed for 30 seconds in the polyethylene bag. The mixture was compression-molded using a tableting machine (HT-AP-18SS-II, manufactured by Hata Tekkosho Co., Ltd., mortar with a diameter of 8.5 mm, punch with a R plane having a radius of curvature of 10 mm) so that the mass was 200 mg, and the molded substance was then crushed using a pestle and a mortar, to obtain a granulated substance. In the resulting granulated substance, granules which were passed through a 850-μm sieve, and left on a 106-μm sieve were obtained as main drug granules. The main drug granules, microcrystalline cellulose, and low substituted hydroxypropylcellulose were then mixed for 3 minutes in a polyethylene bag. To the mixture, magnesium stearate was added, and the mixture was mixed for 30 seconds in the polyethylene bag. The mixture was pressed into a tablet using a tableting machine (HT-AP-18SS-II, manufactured fey Hata Tekkosho Co., Ltd., mortar with a diameter of 8.5 mm, punch with a R plane having a radius of curvature of 10 mm) so that the mass was 250 mg and the thickness of a tablet was 4.2 mm, to obtain a tablet.

(Test Example 1) Dissolution Test (First Fluid for Dissolution Test)

Figure 3:
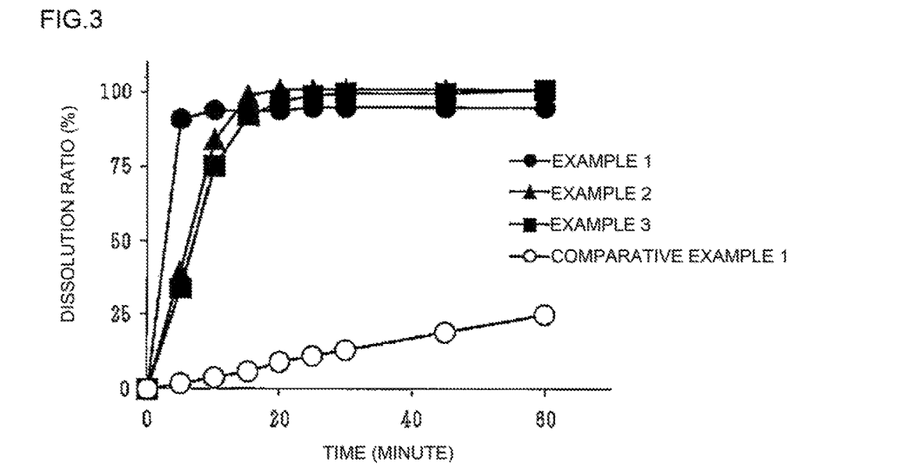
FIG. 3 shows results of a dissolution test of tablets obtained immediately after production in Examples 1 to 3 and Comparative Example 1 (dissolution media: first fluid for dissolution test).

In order to evaluate each of the compositions (tablets) in Examples and Comparative Examples, a dissolution test was performed in accordance with dissolution apparatus 2 (paddle method) in the Japanese Pharmacopoeia Sixteenth Edition. Detailed conditions of the dissolution test are as follows. The results of the dissolution test are shown in FIG. 3.

Paddle rotation speed: 50 rpm
Temperature of test media: 37° C.
Test media: 900 mL of first fluid for dissolution test in the Japanese Pharmacopoeia Sixteenth Edition In the tablet containing no salting-out agent in Comparative Example 1, the dissolution property is very poor, and the dissolution rate after 60 minutes is 25% or less. This is considered because Compound 1 on a surface of the tablet is gelled by contact with water, and rapid permeation of water into the inside of the tablet is inhibited. When the residue after the dissolution test was observed, it was visually confirmed that a solution was not permeated into the inside of the tablet, and disintegration of the tablet was not caused.

In contrast, in the tablets in Examples 1 to 3 which contain a salting-out agent such as L-glutamic acid hydrochloride (Example 1), monobasic sodium citrate (Example 2), and dibasic sodium citrate (Example 3), the dissolution rate was significantly improved. In all the tablets in Examples 1 to 3, the dissolution rate after 10 minutes exhibited 70% or more, and the dissolution rate after 60 minutes exhibited about 90% (FIG. 3). In Examples 1 to 3, the salting-out agent was contained in the main drug granules. The salting-out agent may be contained outside the main drug granules.

Example 4

In accordance with prescription described in Table 2, Compound 1 and lactose hydrate were mixed for 3 minutes in a polyethylene bag. To the mixture, magnesium stearate was added, and the mixture was mixed for 1 minute in the polyethylene bag. The mixture was compression-molded using ROLLER COMPACTOR (TF-MINI, manufactured by Freund Corporation, roll pressure: 70 kgf, roll rotation speed: 3 $min^{-1}$), and subjected to size adjustment using ROLL GRANULATOR (GRH-T-54-S, manufactured by

TABLE 1

| COMPONENT | EXAMPLE 1 | EXAMPLE 2 | EXAMPLE 3 | COMPARATIVE EXAMPLE 1 |
|---|---|---|---|---|
| COMPOUND I | 108.3 | 108.3 | 108.3 | 108.3 |
| L-GLUTAMIC ACID HYDROCHLORIDE | 21.6 | — | — | — |
| MONOBASIC SODIUM CITRATE | — | 21.6 | — | — |
| DIBASIC SODIUM CITRATE | — | — | 21.6 | — |
| MICROCRYSTALLINE CELLULOSE | 17.1 | 17.1 | 17.1 | 38.7 |
| MAGNESIUM STEARATE | — | — | — | — |
| SODIUM STEARYL FUMARATE | 3 | 3 | 3 | 3 |
| SUBTOTAL (mg) | 150 | 150 | 150 | 150 |
| MICROCRYSTALLINE CELLULOSE* | 73.2 | 73.2 | 73.2 | 73.2 |
| LOW SUBSTITUTED HYDROXYPROPYLCELLULOSE* | 25 | 25 | 25 | 25 |
| MAGNESIUM STEARATE* | 1.8 | 1.8 | 1.8 | 1.8 |
| TOTAL (mg) | 250 | 250 | 250 | 250 |

*Added after granulation

Nippon Granulator Co., Ltd.), to obtain a granulated substance (using four kinds of roils with pitch widths of 6 mm, 2 mm, 1.2 mm, and 0.6 mm). The resulting granulated substance was passed through a 850-μm sieve, to obtain a sieved product as main drug granules. The main drug granules, microcrystalline cellulose, low substituted hydroxypropylcellulose, and monobasic sodium citrate passed through a sieve with an opening of 212 μm were then mixed for 3 minutes in a polyethylene bag. To the mixture, magnesium stearate was added, and the mixture was mixed for 1 minute in the polyethylene bag. The mixture was pressed into a tablet using a tableting machine (HT-AP-18SS-II, manufactured by Hata Tekkosho Co., Ltd., mortar with a diameter of 8.5 mm, punch with a R plane having a radius of curvature of 10 mm) so that the mass was 250 mg and the thickness of a tablet was 4.2 mm, to obtain a tablet.

Comparative Example 2

In accordance with prescription described in Table 2, the same operation as that in Example 4 was performed except that monobasic sodium citrate was not used, to obtain a tablet.

TABLE 2

| COMPONENT | EXAMPLE 4 | COMPARATIVE EXAMPLE 2 |
|---|---|---|
| COMPOUND 1 | 108.3 | 108.3 |
| LACTOSE HYDRATE | 39.45 | 39.45 |
| MAGNESIUM STEARATE | 2.25 | 2.25 |
| SUBTOTAL (MAIN DRUG GRANULES) | 150 | 150 |
| MICROCRYSTALLINE CELLULOSE | 37.75 | 73.75 |
| LOW SUBSTITUTED HYDROXYPROPYLCELLULOSE* | 25 | 25 |
| MONOBASIC SODIUM CITRATE* | 36 | — |
| MAGNESIUM STEARATE* | 1.25 | 1.25 |
| TOTAL (mg) | 250 | 250 |

*Added after granulation (Test Example 2) Disintegration Test (First Fluid for Dissolution Test)

For the tablets obtained in Example 4 and Comparative Example 2, a disintegration test was performed in accordance with the disintegration test in the Japanese Pharmacopoeia Sixteenth Edition. Detailed conditions of the disintegration test are as follows.
Temperature of test media: 37° C.
Test media: first fluid for disintegration test in the Japanese Pharmacopoeia Sixteenth Edition
The results of the disintegration test are shown in Table 3.

TABLE 3

| Run | EXAMPLE 4 | COMPARATIVE EXAMPLE 2 |
|---|---|---|
| 1 | 1' 15" | 58' 25" |
| 2 | 1' 30" | 58' 50" |
| 3 | 1' 35" | 60 MINUTES OR MORE |
| 4 | 1' 35" | 60 MINUTES OR MORE |
| 5 | 1' 40" | 60 MINUTES OR MORE |
| 6 | 1' 45" | 60 MINUTES OR MORE |

The tablet containing no salting-out agent in Comparative Example 2 was not disintegrated after 60 minutes. This is considered because Compound 1 on a surface of the tablet is gelled by contact with water, and rapid permeation of water into the inside of the tablet is inhibited. As seen from a disintegration time in Example 4, a tablet in which a disintegration time within 2 minutes was achieved and disintegration property was highly improved by addition of a salting-out agent such as monobasic sodium citrate was obtained. In Example 4, the salting-out agent was contained outside the main drug granules. However, the salting-out agent may be contained in the main drug granules.

Example 5

In accordance with prescription described in Table 4, Compound 1 crusted for 45 seconds using Wonder Blender (trade name) (WB-1, manufactured by Osaka Chemical Co., Ltd.), sodium chloride crushed using a mortar and a pestle, xylitol, and light anhydrous silicic acid were mixed for 2 minutes in a glass bottle. The mixture was pressed into a tablet using a tableting machine (HT-AP-18SS-II, manufactured by Hata Tekkosho Co., Ltd., mortar with a diameter of 8.5 mm, punch with a R plane having a radius of curvature of 10 mm) so that the mass was as described in Table 4 and the tablet hardness was 5 kg or more, to obtain a tablet.

Example 6

In accordance with prescription described in Table 4, the same operation as in Example 5 was performed to obtain a tablet.

TABLE 4

| COMPONENT | EXAMPLE 5 | EXAMPLE 6 |
|---|---|---|
| COMPOUND 1 | 108.3 | 108.3 |
| XYLITOL | 219.4 | 219.4 |
| LIGHT ANHYDROUS SILICIC ACID | 0.7 | 0.7 |
| SODIUM CHLORIDE | 21.6 | 43.2 |
| TOTAL | 350 | 371.6 |

(Test Example 3) Dissolution Test (First Fluid for Dissolution Test)

Figure 4:
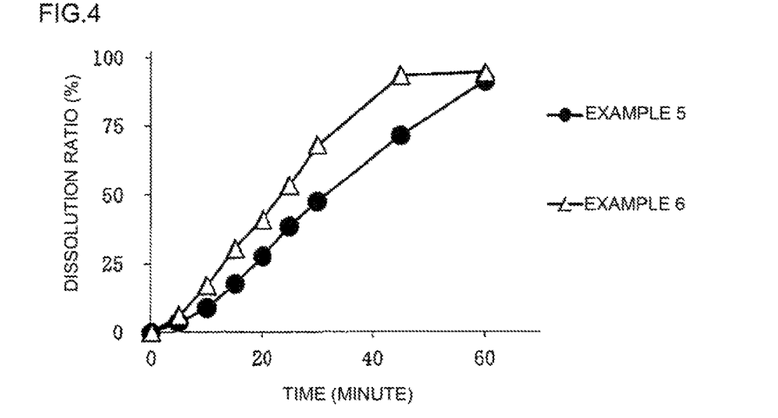
FIG. 4 shows results of a dissolution test of tablets obtained immediately after production in Examples 5 to 6 (dissolution media: first fluid for dissolution test).

A dissolution test was performed in the same manner as in Test Example 1. The results of the dissolution test are shown in FIG. 4.

In prescriptions of Examples 5 and 6, only the amount of a salting-out agent was different. As seen from the results of FIG. 4, when the amount of the salting-out agent is increased, the dissolution rate is improved. In Examples 5 and 6, preparations were prepared, by a direct compression method. The preparations prepared by the direct compression method also exert an effect of suppressing gelation of the salting-out agent.

Example 7

In accordance with prescription described in Table 5, Compound 1 crushed for 45 seconds using bonder Blender (trade name) (WB-1, manufactured by Osaka Chemical Co., Ltd.), sodium chloride crushed using a mortar and a pestle, and isomalt were mixed for 2 minutes in a glass bottle. The mixture was pressed into a tablet using a tableting machine (HT-AP-18SS-II, manufactured by Hata Tekkosho Co., Ltd., mortar with a diameter of 8.5 mm, punch with a R plane having a radius of curvature of 10 mm) so that the mass was as described in Table 5 and the tablet hardness was 5 kg or more, to obtain a tablet.

Example 8

In accordance with prescription described in Table 5, the same operation as in Example 7 was performed to obtain a tablet.

Example 9

In accordance with prescription described in Table 5, the same operation as in Example 7 was performed to obtain a tablet.

TABLE 5

| COMPONENT | EXAMPLE 7 | EXAMPLE 8 | EXAMPLE 9 |
|---|---|---|---|
| COMPOUND 1 | 108.3 | 108.3 | 108.3 |
| ISOMALT | 20.1 | 70.1 | 120.1 |
| SODIUM CHLORIDE | 21.6 | 21.6 | 21.6 |
| TOTAL | 150 | 200 | 250 |

(Test Example 4) Dissolution Test (First Fluid for Dissolution Test)

Figure 5:
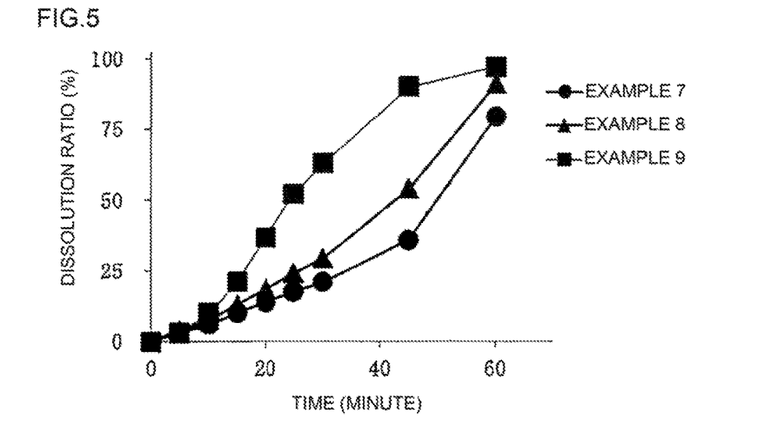
FIG. 5 shows results of a dissolution test of tablets obtained immediately after production in Examples 7 to 9 (dissolution media: first fluid for dissolution test).

A dissolution test was performed in the same manner as in Test Example 1. The results of the dissolution test are shown in FIG. 5.

When the tablet is prepared by the direct compression method, rapid dissolution that is exerted by a tablet produced by a granulation method is not exerted (see FIG. 3). However, when a sugar alcohol such as isomalt is used as an excipient and the amount of the sugar alcohol is increased, an effect of improving a dissolution rate is confirmed (Examples 7 to 9).

Reference Example 1

In accordance with prescription described in Table 6, Compound 1 and microcrystalline cellulose were mixed for 3 minutes in a polyethylene bag. The mixture was pressed into a tablet using a tableting machine (HT-AP-18SS-II, manufactured by Hata Tekkosho Co., Ltd., mortar with a diameter of 8.5 mm, punch with a R plane having a radius of curvature of 10 mm) so that the mass was 250 mg and the tablet pressing pressure was 1,000 kgf, to obtain a tablet.

Reference Example 2

In accordance with prescription described in Table 6, Compound 1 and isomalt were mixed for 3 minutes in a polyethylene bag. The mixture was pressed into a tablet using a tableting machine (HT-AP-18SS-II, manufactured by Hata Tekkosho Co., Ltd., mortar with a diameter of 8.5 mm, punch with a R plane having a radius of curvature of 10 mm) so that the mass was 250 mg and the tablet pressing pressure was 1,000 kgf, to obtain a tablet.

Reference Example 3

In accordance with prescription described in Table 6, Compound 1 and lactose hydrate were mixed for 3 minutes in a polyethylene bag. The mixture was pressed into a tablet using a tableting machine (HT-AP-18SS-II, manufactured by Hata Tekkosho Co., Ltd., mortar with a diameter of 8.5 mm, punch with a R plane having a radius of curvature of 10 mm) so that the mass was 250 mg and the tablet pressing pressure was 1,000 kgf, to obtain a tablet.

Reference Example 4

In accordance with prescription described in Table 6, Compound 1 and mannitol were mixed for 3 minutes in a polyethylene bag. The mixture was pressed into a tablet using a tableting machine (HT-AP-18SS-II, manufactured by Hata Tekkosho Co., Ltd., mortar with a diameter of 8.5 mm, punch with a R plane having a radius of curvature of 10 mm) so that the mass was 250 mg and the tablet pressing pressure was 1,000 kgf, to obtain a tablet.

TABLE 6

| COMPONENT | REFERENCE EXAMPLE 1 | REFERENCE EXAMPLE 2 | REFERENCE EXAMPLE 3 | REFERENCE EXAMPLE 4 |
|---|---|---|---|---|
| COMPOUND 1 | 108.3 | 108.3 | 108.3 | 108.3 |
| MICROCRYSTALLINE CELLULOSE | 141.7 | — | — | — |
| ISOMALT | — | 141.7 | — | — |
| LACTOSE HYDRATE | — | — | 141.7 | — |
| MANNITOL | — | — | — | 141.7 |
| TOTAL | 250 | 250 | 250 | 250 |

(Test Example 5) Stability Test

Each of the tablets in Reference Examples 1 to 4 was placed in a glass bottle, and stored in an opened state and a sealed state under a condition of 40° C. and 75% RH for 4 weeks. The content of 7-{(3S,4S)-3-aminomethyl-4-fluoro-pyrrolidine-1-yl}-6-fluoro-1-(2-fluoroethyl)-8-methoxy-4-oxo-1,4-dihydroquinoline-3-carboxylic acid (Compound 2) and the content of Compound 1 after the storage were measured through liquid chromatography, and the content of Compound 1 was represented as a percentage relative to the content of Compound 1.

Test Condition by Liquid Chromatography

Column: a separation column in which each stainless tube with an inner diameter of 4.6 mm and a length of 150 mm was charged with octadecyl-silylated silica gel of 3 μm for liquid chromatography (GL Sciences Inc., Inertsil ODS-3).

A liquid: liquid in which 2.16 g of sodium 1-octanesulfonate was dissolved in diluted phosphoric acid (1→1,000) in a volume of 1,000 mL.

B liquid: methanol for liquid chromatography

Liquid sending: The mixed ratio of A liquid and B liquid was changed to control the concentration gradient.

Detector: Ultraviolet absorption spectrophotometer (measurement wavelength: 294 nm)

Retention time of Compound 2 relative to Compound 1: 0.70

The results of the stability test in Reference Examples 1 to 3 are shown in Table 7, For the tablets containing isomalt (Reference Example 2), lactose hydrate (Reference Example 3), or mannitol (Reference Example 4), a trend of suppressing production of a decomposed substance was confirmed, as compared with the tablet containing microcrystalline cellulose (Reference Example 1).

TABLE 7

| STORAGE CONDITION | REFERENCE EXAMPLE 1 | REFERENCE EXAMPLE 2 | REFERENCE EXAMPLE 3 | REFERENCE EXAMPLE 4 |
|---|---|---|---|---|
| CONTENT OF COMPOUND 2 (AT TIME OF INITIATION) % | N.D. | N.D. | N.D. | N.D. |
| CONTENT OF COMPOUND 2 (AFTER STORAGE IN OPENED STATE) % | <0.05 | <0.05 | N.D. | N.D. |
| CONTENT OF COMPOUND 2 (AFTER STORAGE IN SEALED STATE) % | 0.08 | N.D. | N.D. | N.D. |

INDUSTRIAL APPLICABILITY

A novel pharmaceutical composition which can suppress delayed release of the compound represented by general formula (1) or the salt thereof can be provided by using a salting-out agent.

The invention claimed is:

1. A solid pharmaceutical composition comprising:
   7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a salt thereof, and
   at least one salting-out agent selected from the group consisting of an inorganic salt, a citric salt and a glutamate.

2. The solid pharmaceutical composition according to claim 1, further comprising a non-cellulosic excipient.

3. The solid pharmaceutical composition according to claim 2, wherein the solid pharmaceutical composition is obtained by compression-molding a mixture comprising:
   (i) a granulated substance comprising the 7-[(3 S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a salt thereof and the non-cellulosic excipient, and
   (ii) the salting-out agent.

4. The solid pharmaceutical composition according to claim 1, further comprising a disintegrant.

5. The solid pharmaceutical composition according to claim 4, wherein the disintegrant is a swelling disintegrant.

6. The solid pharmaceutical composition according to claim 2, wherein the solid pharmaceutical composition is obtained by directly compression-molding a mixture comprising the 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a salt thereof, the non-cellulosic excipient, and the salting-out agent.

7. The solid pharmaceutical composition according to claim 6, wherein the non-cellulosic excipient is a sugar alcohol.

8. The solid pharmaceutical composition according to claim 6, wherein the non-cellulosic excipient is at least one selected from the group consisting of isomalt and xylitol.

9. The solid pharmaceutical composition according to claim 6, wherein the salting-out agent is sodium chloride.

10. The solid pharmaceutical composition according to claim 1, comprising 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid hydrochloride.

11. A method for producing the solid pharmaceutical composition according to claim 2, wherein the solid pharmaceutical composition is a tablet, and wherein the method comprises:
   (i) mixing a granulated substance comprising the 7-[(3 S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a salt thereof and the non-cellulosic excipient with the salting-out agent to obtain a mixture; and
   (ii) compression-molding the obtained mixture.

12. A method for producing the solid pharmaceutical composition according to claim 2, wherein the solid pharmaceutical composition is a tablet, and wherein the method comprises:
   (i) mixing the 7 [(3 S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a salt thereof, the non-cellulosic excipient, and the salting-out agent to obtain a mixture; and
   (ii) compression-molding the mixture.

13. A solid pharmaceutical composition comprising:
   a granular substance comprising 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a salt thereof and a non-cellulosic excipient; and
   at least one salting-out agent selected from the group consisting of an inorganic salt, a citric salt and a glutamate.

14. A solid pharmaceutical composition comprising 7 [(3S,4S)-3-{(cyclopropylamino)methyl}-4-fluoropyrrolidine-1-yl]-6-fluoro-1-(2-fluoroethyl)-8-methoxy-4-oxo-1,4-dihydroquinoline-3-carboxylic acid or a salt thereof, a-non-cellulosic excipient, and at least one salting-out agent selected from the group consisting of an inorganic salt, a citric salt and a glutamate, wherein the composition is uniform.

15. The solid pharmaceutical composition according to claim 1, wherein the salting-out agent is selected from the group consisting of a citric salt, a phosphoric salt, a carbonate, a metal chloride, sodium sulfate, sodium sulfite, sodium bisulfite, sodium hydroxide and a glutamate.

16. The solid pharmaceutical composition according to claim 1, wherein the salting-out agent is selected from the group consisting of a citric salt, a metal chloride and a glutamate.

17. The solid pharmaceutical composition according to claim 1, further comprising at least one non-cellulosic excipient selected from the group consisting of a monosaccharide, a disaccharide, a starch and a sugar alcohol.

* * * * *